United States Patent [19]

Piran

[11] Patent Number: 4,874,710

[45] Date of Patent: Oct. 17, 1989

[54] ASSAY AND PRODUCT IN WHICH BINDER AND LIPOSOMES ARE SUPPORTED ON A SOLID SUPPORT

[75] Inventor: Uri Piran, Norwood, Mass.

[73] Assignee: Becton Dickinson and Company, Franklin Lakes, N.J.

[21] Appl. No.: 831,410

[22] Filed: Feb. 20, 1986

[51] Int. Cl.[4] .................. G01N 33/53; G01N 33/566; G01N 33/543; G01N 33/537
[52] U.S. Cl. ........................................ 436/518; 435/7; 436/501; 436/538; 436/543; 436/808; 436/810; 436/821; 436/829; 530/387; 514/75; 514/76; 514/77; 514/78
[58] Field of Search .................. 435/7; 436/501, 517, 436/518, 524, 531, 538, 543, 808, 810, 821, 829; 530/387; 514/75–78

[56] References Cited

U.S. PATENT DOCUMENTS 3,843,777 10/1974 Hainski et al. .................. 436/522 X
4,517,303  5/1985 Freytag et al. ...................... 436/501
4,622,294 11/1986 Kung et al. ......................... 435/14 X
4,666,830  5/1987 Wagner ..................................... 435/7

*Primary Examiner*—Robert J. Warden
*Assistant Examiner*—Jack Spiegel
*Attorney, Agent, or Firm*—Elliot M. Olstein; John G. Gilfillan, III; John N. Bain

[57] ABSTRACT

In an assay, a conjugate of ligand and sac lysing agent is contacted with analyte and binder to produce bound and unbound portions of conjugate. The unbound portion of the conjugate contacts sacs, containing a detectable marker to release the marker as a measure of analyte. The binder and sacs may be placed on different portions of a solid support to provide a solid phase assay.

16 Claims, No Drawings

ASSAY AND PRODUCT IN WHICH BINDER AND LIPOSOMES ARE SUPPORTED ON A SOLID SUPPORT

This invention relates to an assay for a ligand (analyte) and products used in such assay. More particularly, this invention relates to an assay for an analyte in which the sensitivity of the assay is increased, as well as products used in such assay.

Immunoassay methods, in general, are based on the competition between a specific analyte, the amount of which is to be determined in a sample, and a known amount of the analyte or appropriate analog thereof in labeled form (tracer) for a limited number of available binding sites on a binder which is specific towards the analyte and tracer. Thus, in a system containing an unknown amount of analyte, a known amount of tracer and a limited known amount of binder, the greater the concentration of analyte in the sample, the less the tracer will be bound by the binder.

If the concentration of tracer and binder is fixed and the only variable is the level of analyte, it is possible to establish an assay system for measuring the unknown level of analyte by determining the amount of bound and free tracer in the system. Common labels include radioisotopes, fluorescent dyes, enzymes, chemiluminescent materials, and the like. The activity of the radioisotope, the fluorescent intensity of the dye or the activity of the enzyme on a substrate is compared with the values given by a range of known amounts of the analyte treated in the same manner. The values obtained from the determination of the standard samples are used for establishing a standard calibration curve for the specific system and this curve is then used to determine an unknown concentration of the analyte in a known sample.

In such assays, sensitivity is of prime importance, in that in many cases, it is necessary to measure low analyte levels.

In an attempt to provide more sensitive assays, tracers have been produced for use in the assay wherein the tracer is comprised of the analyte to be assayed or appropriate analog thereof coupled to a sac which includes a detectable marker therein. In such an assay, the amount of marker which can be included in the sac is greater than the amount of marker which can be directly linked to the analyte or appropriate analog thereof, whereby each mole of tracer has in excess of one mole of marker, which increases the sensitivity of the assay. In the case where the tracer is produced from a sac having a marker therein, which is sensitized with the analyte or appropriate analog thereof, there are still limits to the sensitivity in that, in general, only a single sac can be attached to each mole of the analyte or appropriate analog thereof. As a result, there is still a need for further increasing the sensitivity of an assay by amplifying the amount of detectable marker (per mole of analyte or appropriate analog thereof) used in formulating a tracer.

In accordance with one aspect of the present invention, there is provided an assay for an analyte wherein a sample containing an analyte is contacted with a binder for at least the analyte in the presence of a conjugate comprised of a ligand coupled to a sac lysing agent. The ligand of the conjugate is bound by one of the analyte and binder. The amount of conjugate which is bound to the binder is dependent upon the amount of analyte in the sample (the analyte and conjugate compete for binding sites on the binder or the conjugate is bound to the binder through the analyte). The assay is effected in a manner such that conjugate, which is not bound to the binder (directly or indirectly) comes into contact with sacs including a detectable marker. As a result of such contact with unbound conjugate, the lysing agent attached to the ligand lyses the sacs, thereby releasing marker. Since the amount of conjugate available for lysing of the sacs (free conjugate) is dependent upon the amount of analyte present in the sample, the amount of marker which is released from the sacs and/or the rate at which the marker is released, is indicative of the amount of analyte in the sample.

Thus, by proceeding in accordance with the present invention, each conjugate molecule which is not bound directly or indirectly to the binder is capable of releasing a large number of marker molecules to thereby increase the overall sensitivity of the assay.

More particularly, in accordance with the one aspect of the present invention, the tracer used in the assay is actually formed from two separate and distinct components, with one component being the conjugate comprised of ligand and lysing agent, and the other component being the sacs which include a detectable marker therein. In accordance with this aspect of the present invention, the amount of lysing agent which is available for lysing the sacs is proportional to the amount of analyte in the sample, and the amount of marker and/or the rate at which the marker is released from the sacs in proportional (directly or indirectly depending on the assay format) to the amount of lysing agent (unbound conjugate) which is available for lysing of the sacs.

In accordance with a preferred aspect of the present invention, the assay is effected as a solid phase assay with the binder supported on an appropriate solid support. In such an assay, the bound conjugate is not free to move through the assay medium, whereas the unbound conjugate is free to move through the assay medium. As a result, the bound conjugate has no essential contact with the sacs containing the detectable marker, whereby contact between the sacs containing the detectable marker, and the lysing agent forming a part of the conjugate, is dependent upon the amount of unbound conjugate present in the assay medium. Thus, a portion of the conjugate is immobilized in the assay medium by being bound to the supported binder (conjugate bound directly to the supported binder or conjugate bound to analyte bound to the supported binder) to provide both a free and bound portion of conjugate, with the free portion of the conjugate determining the amount and/or rate of release of marker from the sac. As hereinabove indicated the amount of the free portion of the conjugate which is present in the assay medium is proportional to the amount of analyte present in the sample being assayed.

In accordance with a particularly preferred embodiment of the invention, the sacs containing a detectable marker and the binder used in the assay are both supported on a solid support, preferably the same solid support. If on the same support, the sacs and binder are spaced from each other in a manner such that essentially only the unbound conjugate is available for lysing of the sacs. When contacted with the assay medium containing the analyte, essentially only the free (unbound) portion of the conjugate is available for contact with the supported sacs containing the detectable marker.

The hereinabove preferred embodiment is particularly suitable for use in a "dip-stick" type of assay wherein both sacs and binder are immobilized on different portions of the "dip-stick", and the "dip-stick" is inserted into an assay medium which contains the analyte to be assayed, and which may also include the conjugate.

In a preferred form of the invention, both the binder and sac are immobilized on the solid support, preferably a "dip-stick", with the conjugate also being supported on the solid support by being bound to the binder. When such a solid support is contacted with an assay medium containing the analyte to be assayed, the amount of conjugate which is displaced from the binder is directly proportional to the amount of analyte in the sample, whereby the amount of conjugate which is available in the assay medium for contacting the immobilized sacs, containing a detectable marker, is directly proportional to the amount of analyte present in the sample.

The sacs, which includes a marker in the interior thereof, which are employed in the assay may be any one of a wide variety of sacs, which can be lysed by a sac lysing agent. Such sacs are generally known in the art, and include liposomes (sometimes called vesicles), polymer microcapsules (for example, those made by coaservation, or interfacial polymerization), etc. As should be apparent, the sac employed in the assay is coordinated with the sac lysing agent attached to the ligand forming the conjugate, so that the sac is lysed or ruptured upon contact with the sac lysing agent.

Polymer microcapsules are produced by procedures known in the art, except that the solution in which the microcapsules are formed also include a marker whereby the interior of the polymer microcapsule includes the marker. The preparation of such microcapsules is disclosed for example in *Microencapsulation Process and Applications*, edited by Jan E. Vandegger (Plenum Press 1974).

As known in the art, liposomes can be prepared from a wide variety of lipids, including phospholipids, glycolipids, steroids, relatively long change alkyl esters; e.g., alkyl phosphates, fatty acid esters, e.g. lecithin, fatty amines and the like. A mixture of fatty materials may be employed such as a combination of neutral steroid, a charged amphiphile and a phospolipid. As illustrative examples of phospholipids there may be mentioned sphingomyelin, dipalmitoyl, lecithin, and the like. As representative steroids, there may be mentioned cholesterol, cholestanol, Ianosterol, and the like. As representative examples of charged amphiphilic compounds, which generally contain from 12 to 30 carbon atoms, there may be mentioned mono-or dialkyl phosphate ester, quaternary ammonium salts, or an alkylamine; e.g., dicetyl phosphate, stearyl amine, hexadecyl amine, dilauryl phosphate, dioctadecyl sulfonate, didodecyl dioctylammonium formide, and the like.

The liposome sacs are prepared in an aqueous solution including the marker, whereby the sacs will include the marker in the interior thereof. The liposome sacs are easily prepared by vigorous agitation in the solution, followed by removal of the marker from the exterior of the sac.

Further details with respect to the preparation of sacs are set forth in U.S. Pat. No. 4,342,826 and PCT International Publication No. WO80/01515, as well. "Liposomes: From Physical Structure to Therapeutic Applications," C. G. Knight, Ed. Elsevier, 1981, and "Membrane Mimetic Chemistry" by Janos H. Fendler. John Wiley and Sons, 1982 all of which are hereby incorporated by reference.

The sac lysing agent may be any one of a wide variety of materials which is capable of lysing the sac employed in the assay, with the particular sac lysing agent employed being dependent upon the sacs employed in the assay. The preferred lysing agent is an enzyme, and the enzymes capable of lysing different sacs would be known to those skilled in the art. Thus, for example, phospholipases and alkaline phosphatase are suitable enzymatic lysing agents. A protease enzyme is known to be effective for lysing a gelatine microcapsule The marker which is included within the sac may be any one of a wide variety of detectable markers, including but not limited to, radioisotopes, enzymes (in the use of an enzyme, the marker and lysing agent should be different enzymes), a chromogen (an absorbing dye or a fluorescent material), a luminescent compound, spin labels, etc. Such detectable markers, and the methods for determining the markers are generally known in the art, and no further details in this respect are deemed necessary for a complete understanding of the invention. Representative examples of preferred types of markers are:

a. Dyes with a high extinction coefficient, such as sulforhodamine B and copper phthalocyanine tetrasulfonic acid, and oxazine 4 perchlorate.

b. Fluorescent dyes, such as carboxyfluorescein, organic chelates of europium and terbium, various coumarins and rhodamines.

c. Enzymes other than the lysing enzymes, such as horseradish peroxidase, which can be determined, after lysis, by a colorimetric, fluorescent, luminescent, or electrochemical (amperometric) device.

As hereinabove indicated, the conjugate which is employed in the assay is a ligand having a sac lysing agent, in an active form, coupled thereto. The sac lysing agent is of a type as hereinabove described. The ligand which is employed in producing the conjugate is dependent upon the assay which is employed. Thus, for example, if the assay is for an analyte which is an antigen or a hapten, the ligand portion of the conjugate may be the analyte or appropriate analog thereof or in some cases may be an antibody for the analyte.

As used herein, the term "appropriate analog", when referring to an analog of the analyte, means that the analog of the analyte is bound by the binder for the analyte which is used in the assay. If the analyte is an antibody, the ligand portion of the conjugate may be an antigen bound by the antibody or an antibody elicited in response to the analyte or the antibody.

The ligand portion of the conjugate is bound by one of the binder or the analyte. Thus, for example, in a so called "sandwich" assay, the analyte may be bound by the binder and the conjugate bound by the analyte, whereby the amount of conjugate bound to the binder through the analyte is dependent on the amount of analyte in the sample.

The above types of assays and others should be apparent to those skilled in the art from the teachings herein.

The ligand portion of the conjugate may be coupled to the lysing agent by procedures which are generally known in the art for coupling one compound to another. Thus, for example, the lysing agent may be coupled to the ligand portion of the conjugate by covalent coupling, derivitization, activation, and the like.

The lysing agent may be coupled to the ligand portion of the conjugate by the use of an appropriate coupling or spacer compound (one that does not destroy the immunoreactivity of the ligand, or the sac lysing activity of the lysing agent). As known in the art, the coupling compound has two reactive functional groups, one of which functional groups is capable of reacting or being linked to a functional group of the ligand portion of the conjugate, and the other of which is capable of reacting or being linked to a functional group on the sac lysing agent. For example, the spacer or coupling compound, which includes at least two reactive substituent groups, may contain either a carboxyl, isocyanate, isothiocyanate, amino, thiol, hydroxy, sulfonyl, carbonyl, etc., substitutent group, which, as should be apparent, is dependent upon the functional group present in the ligand and lysing agent which are to be coupled to each other.

Alternatively, the sac lysing agent may be coupled directly to the ligand. Thus, for example, if the ligand portion of the conjugate has an amino substituent group, and the sac lysing agent portion of the conjugate has a carbonyl or carboxyl substituent group, then the ligand and sac lysing agent may be directly conjugated to each other by procedures known in the art; for example, an active ester technique.

The binder which is used in the assay is one which is specific for the analyte. In the case where the analyte is an antigen or a hapten, the binder may be an antibody or a naturally occurring binder which is specific for the analyte. In the case where the analyte is an antibody, then the binder employed in the assay may be either an antigen or an antibody elicited in response to the antibody to be assayed, whereby the binder is specific for the analyte.

As hereinabove indicated, in accordance with one aspect of the present invention, at least the binder may be supported on a solid support, and in a particularly preferred embodiment, both the binder and the sacs including the detectable marker are both supported on a solid support, preferably the same solid support, although it is possible to have each supported on a different support present in the assay medium. The solid supports which may be employed are any one of a wide variety of solid supports which are capable of supporting the binder; in accordance with a preferred embodiment, the support is also capable of supporting the sacs. As representative examples of suitable supports, there may be mention various polymers such as polypropylene, polystyrene, polyacrylamide, etc.; glass beads; celluose; bacterial cells; etc. Solid supports are generally known in the art, and as a result, no further disclosure in this respect is deemed necessary for a complete understanding of the present invention.

The binder may be supported on the solid support by procedures generally known in the art. In some cases, depending on the support, the binder may be adsorbed onto the support. In other cases, it may be necessary to employ covalant coupling for supporting the binder on the support.

The sacs may be supported on a solid support by a variety of procedures. For example, the sac may be derivatized with biotin by procedures known in the art (for example, forming the sac from a material having biotin conjugated thereto or derivatizing the formed sac with biotin) and the solid support coated with avidin whereby the sac is supported on the solid support by binding of avidin and biotin.

As another procedure, the sac may be derivatized with an antigen or hapten and the solid supported coated with the appropriate antibody whereby the sac is supported on the solid support by binding between the antigen or hapten and the antibody. For example, the sac may be derivatized with digoxin or dinitrophenol and the solid support coated with the appropriate antibody, whereby the sac is supported on the solid support by binding of the digoxin or dinitrophenol to its antibody.

These and other procedures should be apparent to those skilled in the art from the teachings herein.

As hereinabove indicated, if the binder used in the assay and the sacs are to be supported on the same solid support, then separate and distinct portions of the support are used for supporting the sacs and binder to be used in the assay. For example, one portion of the support would be coated with the assay binder, and a separate and distinct portion of the sac is coated with a binder (for example avidin) for binding the sac (sac derivatized with biotin).

In the case where the solid support contains the sac, the solid support is preferably maintained in contact with a suitable aqueous buffer, prior to use in the assay, so as to maintain the integrity of the sac. For example, if the solid support is a tube, the tube may be filled with a buffer.

The solid support may take a wide variety of forms. Thus, for example, the support may be in sheet form, in the form of a tube, in the form of particles, etc. Such various forms are known in the art, and no further details in this respect are deemed necessary for a complete understanding of the invention. As hereinabove indicated, however, a preferred form of the support is a "dip-stick" or sheet which is capable of being inserted into and withdrawn from an assay medium.

The assay of the present invention may be employed for determining a wide variety of analytes, and has particular applicability to those analytes which are generally found in low concentrations in the material to be assayed. As representative examples of such analytes, there may be mentioned:

Cardiac glycosides, such as digoxin and digitoxin. Antiasthmatics, such as theophyllin. Antibiotics, such as gentamicin and tobramycin. Antineopolastics, such as methotrexate. Anticonvulsants, such as phenobarbital, carbamezapine and valparic acid. Antiarrythmics, such as lidocaine and quinidine. Hormones, such as T4, T3, hCG, TSH, and various steroids. The invention is not limited to the representative examples.

As hereinabove indicated in accordance with a preferred embodiment of the present invention, at least the binder used in the assay is supported on a solid support so as to bind a portion of the conjugate (such portion may be directly bound or indirectly bound to the binder) to provide a free or unbound portion of the conjugate for contacting the sacs containing the detectable marker, with the assay being accomplished in a manner such that the amount of unbound conjugate is proportional to the amount of analyte in the sample.

In employing a supported binder, it may be possible to incubate the sample containing the analyte (ligand to be assayed), and the conjugate in the presence of a supported binder in an assay medium including the sacs containing the detectable marker. In such a procedure, the rate of lysing is a function of the concentration of the free conjugate in that the bound conjugate does not freely move through the assay medium. Although the sacs are free to move in the assay medium, and are therefore theoretically free to move into contact with bound conjugate to initiate lysing of the sacs by bound conjugate, as a practical matter, the probability of such an event is believed to be small whereby the lysing rate of the sacs is a function of the concentration of free conjugate in the assay medium. In some cases, it may be advantageous to add the sacs after the initial incubation to form the free and bound conjugate fractions, or in the alternative, to separate the free fraction from the bound fraction, and then contact the free fraction with the sacs including the detectable marker.

In accordance with one aspect of the assay of the present invention, a sample containing or suspected of containing the analyte is incubated with a conjugate, which is the analyte or appropriate analog thereof coupled to a sac lysing agent, and a supported binder specific for both the analyte and conjugate. The incubation results in competition between the conjugate and analyte for binding sites on the binder, with the amount of conjugate which is bound to the binder being inversely proportional to the amount of analyte in the sample.

The bound and free components are separated from each other, and the free portion is then contacted with sacs, which include the marker therein, under conditions which prevent premature rupturing of the sacs (the sacs are only ruptured by contact with lysing agent which is exterior to the sacs). This portion of the assay is generally run in an appropriately buffered aqueous medium which is isotonic with the osmolarity of the sacs. Thus, conditions of temperature, pH and ionic concentration are controlled to prevent premature rupturing of the sacs. Thus, for example, an aqueous buffered medium is provided which is isotonic with the osmolarity of the sacs. In general, the buffer provides a pH in the order of from 5 to 9.

As a result of the contact with the lysing agent portion of the conjugate, the sacs are ruptured to release marker. The rate at which marker is released into the medium is dependent upon the concentration of conjugate present, with an increasing amount of conjugate resulting in an increase in the rate of release of marker into the medium. Thus, by determining the rate at which marker is released into the medium, or in the alternative, by determining the amount of marker in the medium after a fixed period of time, and comparing such values with those obtained by an identical procedure using known amounts of analytes (standard analytes having known concentration), there can be obtained a measurement of the amount of analyte present in the sample.

The rate can be determined either kinetically by measuring the signal intensity increase with time, or by the end-point method, where the reaction is allowed to proceed for a fixed length of time, and it is then stopped (for example, by increasing the pH), and the color (or fluorescence, or luminescence, as the case may be) is measured. The higher the reaction rate, the stronger will be the signal at the end-point.

The sample volume which is used in the assay is selected so as to prevent a "run-away" rate for release of the marker, i.e., to provide a detectable rate of change with time. Thus, as the expected analyte concentration increases, the sample volume is decreased so as to provide for a detectable change in rate.

In a preferred embodiment, the binder may be supported on a solid support such as the walls of a tube, and in such a case, the bound and free portions of the conjugate need not be separated from each other. More particularly, the sample containing or suspected of containing the analyte and the conjugate would be initially added to the tube containing the supported binder, followed by addition of sacs of the type hereinabove described. In such an assay, the conjugate which becomes bound to the binder on the walls of the tube would not be free to move through the assay medium to contact the sacs, whereby the rate of release of marker from the sacs would be dependent upon the amount of free conjugate in the assay medium.

In accordance with a further embodiment, a conjugate of a type hereinabove described may be initially bound to binder supported on a solid support, such as the walls of a tube. In such a case, the sample containing or suspected of containing the analyte, as well as the sacs of the type hereinabove described, may be simultaneously added to the tube. In such an embodiment, the analyte in the sample displaces conjugate from the binder, with the amount of conjugate displaced from the binder being directly proportional to the amount of analyte in the sample. In this embodiment, the conjugate displaced from the binder comes into contact with the sacs to release a marker into the assay medium.

It may also be possible to employ a homogeneous assay in the case where the lysing agent used in the conjugate is inactivated when the conjugate is bound to the binder. Thus, for example, in an assay for digoxin which employs an antibody as a binder and a phospholipase as the enzymatic lysing agent bound to the ligand portion of the conjugate, the phospholipsase is sterically hindered when bound to the antibody, whereby the bound conjugate is not available for lysing sacs, whereas the unbound conjugate is capable of lysing sacs to release detectable marker from the sacs.

In accordance with a particularly preferred embodiment, both the binder and the sacs containing the detectable marker are bound to a solid support, preferably the same solid support. The conjugate may be bound to the binder on the solid support or added as a separate component during the assay procedure. In accordance with a preferred embodiment, the conjugate is bound to the binder on the solid support. In such an assay procedure, in the case where, for example, the solid support is the wall of a tube, in such an assay, it is only necessary to add the sample which is to be assayed for the analyte. In this procedure, analyte present in the sample displaces conjugate, and the conjugate which is released from the binder is free to move through the assay medium and contact the sacs which are supported on the solid support to effect lysing thereof and release of marker. The amount and/or rate of release of marker is measured to determine the amount of analyte and/or present of analyte in the sample by use of standard calibrations, prepared by procedures generally known in the art.

As hereinabove indicated, in accordance with another preferred embodiment, both the binder and the sacs are supported on a sheet, preferably in the form of a "dip-stick". In a particularly preferred embodiment the conjugate is bound to the binder supported on a solid support. In accordance with the preferred embodiment, the sheet or "dip-stick" may be introduced into a sample containing the analyte to be assayed, whereby the assay may be accomplished in a homogeneous fashion, and without the necessity of adding reagents to the assay medium.

In accordance with another aspect of the present invention, there is provided a product useful in the assay of an analyte comprised of both a binder for the analyte, and a sac including the detectable marker therein supported on a solid support, with the sacs being of the type hereinabove described, and preferably being a liposome. In accordance with a particularly embodiment of this another aspect of the present invention, a conjugate of the type hereinabove described (ligand coupled to a sac lysing agent) is bound to the binder on the solid support.

The solid support may be of the type hereinabove described, and in accordance with a preferred aspect, the solid support is either in the form of a tube, or in the form of a sheet particularly one which may be employed as a "dip-stick".

Such product may be used in an assay in the manner hereinabove described.

In accordance with a further aspect of the invention, there is provided a reagent kit or package for accomplishing an assay for an analyte, which includes: (a) a conjugate comprised of the analyte to be assayed or appropriate analog thereof conjugated to a sac lysing agent; (b) sacs which include in the interior thereof a detectable marker; and (c) a binder for the analyte. The sac lysing agent which forms a portion of the conjugate is one which is capable of lysing the sacs included in the kit. The binder is preferably supported on a solid support, as hereinabove described. In accordance with a particularly prefered aspect, both the binder and the sacs including a detectable marker (preferably liposomes) are supported on the same solid support and the conjugate may be bound to the binder on the solid support. The components of the kit may be included in the kit or package in separate containers; for example, vials; however, in some cases one or more of the components may be combined into a single vial. The kit may also include other components such as standards of the analyte (analyte samples having known concentrations of the analyte), known buffers, and the like.

In accordance with still a further aspect of the present invention, there is provided sacs, preferably liposomes, which include a detectable marker in the interior thereof, which sacs are supported on a solid support, preferably a solid support which is in the form of a tube, or in the form of a sheet like substrate such as a "dip-stick". Such a product may be employed in an assay of the type hereinabove described. Thus, for example, in the case where the binder is supported on the walls of a tube, after the binder is contacted with both conjugate and sample containing the analyte to be assayed, the sacs containing the detectable marker supported on a sheet, such as a dip-stick may be inserted into the assay medium in the tube. In accordance with another embodiment, in the case where bound and free portions of the conjugate are separated from each other; for example, by pouring the assay medium from a tube which includes the binder supported on the walls of the tube into another container, such separated assay medium, which includes the unbound portion of the conjugate, may be poured into a container (tube) which has the sacs, including a detectable marker therein, supported on the walls of the tube.

The above uses and others for such a product should be apparent to those skilled in the art from the teachings herein.

The invention will be further described with respect to the following examples; however, the scope of the invention is not to be limited thereby:

EXAMPLE

A. 132 umoles chlolesterol, 113 umoles distearoylphosphatidylcholine, 13.2 umoles distearoylphosphatidylglycerol, and 200 ugram distearoylophosphatidylethanolaminebiotin conjugate were dissolved in 20 ml chloroform-methanol (9:1 v/v). The mixture was dried in a 250 ml size round bottom flask using a rotary evaporator at 37° C. The dried lipid film was further dried in-vaccuo at 25° C. for 16 hours and swollen in 2.7% (w/v) glycerol solution containing 1 mM EDTA and 0.02% $NaN_3$ at pH 6.7. Swelling was achieved by gentle swirling at 60° C. for 3 minutes. The turbid liposome suspension was spun for 10 minutes at 2000 rpm to sediment large multilamellar vesicles and the supernatant was collected and spun for 30 minutes at 30,000 rpm to sediment the large unilamellar vesicles. Loading the vesicles with dye was achieved by resuspending the empty liposome pellet in 20 ml of 0.1M solution of sulforhodamine-B at pH 6.7 and extruding the suspension sequentially through polycarbonate membranes of 1.0 u, 0.4, u, and 0.2 pore sizes. Thirty ml of buffer containing 20 mM Tris, 20 mM EDTA, 2% (w/v) glycerol, 0.05% DMSO, and 0.02% $NaN_3$ were added, and the liposomes were spun for 30 minutes at 30,000 rpm. The pellet was resuspended and washed twice in the same buffer to remove unencapsulated dye, and the washed loaded liposomes were diluted in the same buffer at 1 umole phospholipid phosphorous per ml.

(B) A first portion of a polypropylene tube is coated with sheep anti LCG (8 ug/ml) and a second portion of the tube is coated with avidin (5 ug/ml), each in a carbonate buffer (o./m carbonate, pH 9.6).

(C) The liposomes prepared in A are conjugated to the avidin coated portion of the tube, and the tube is filled with an aqueous buffer (Tris HCl buffer pH 7.2, osmotically adjusted to the liposomes).

(D) In an assay for LCG the tracer is LCG conjugated to phospholipase C, by procedures known in the art.

100 ul of sample is added to the buffered tube, followed by addition of the tracer (1 ug). After incubation at 37° C. for 1 hr, the tube is read colorimetrically or fluorimetrically and compared to appropriate standards.

The present invention is particularly advantageous in that it is possible to provide an improved assay format which utilizes sacs including a detectable marker to amplify signal. In addition, it is possible to provide a solid phase assay in which essentially all of the components of the assay are included on a solid support whereby only sample need be added. These and other advantages should be apparent to those skilled in the art.

Numerous variations and modifications of the present invention are possible in light of the above teachings and, therefore, within the scope of the appended claims, the invention may be practiced otherwise than as particularly described.

What is claimed is:

1. An assay for an analyte, comprising:
contacting an analyte with a binder for at least the analyte in the presence of a conjugate, said conjugate comprising a ligand coupled to a liposome lysing agent; said ligand portion of the conjugate being bound by one of the analyte and binder, whereby a portion of the conjugate is bound to the binder; contacting unbound conjugate with liposomes which include in the interior thereof a detectable marker, said binder and liposomes being supported on separate portions of a solid support, said contacting lysing the liposomes; and determining marker released from the liposomes by contact with the liposome lysing agent of the unbound conjugate as a measure of analyte.

2. The assay of claim 1 wherein the binder is a binder for both the analyte and conjugate.

3. The assay of claim 2 wherein the conjugate is bound to the binder, prior to contacting with the analyte.

4. The assay of claim 2 wherein the analyte is present in a sample portion.

5. The assay of claim 1 wherein the binder is a binder for the analyte and the conjugate is bound by the analyte whereby a portion of the conjugate is bound to the binder through the analyte.

6. The assay of claim 1 wherein the liposome comprises a phospholipid.

7. The assay of claim 6 wherein the solid support is in the form of a dipstick and the binder and the liposome are supported on separate and distinct portions of the solid support.

8. A product useful in an assay for an analyte, comprising:

a binder for an analyte and liposomes including a detectable marker in the interior thereof, said binder and said liposomes being supported on separate portions of a solid support.

9. The product of claim 8 wherein the support is in the form of a dipstick.

10. The product of claim 9 wherein the binder has bound thereto a ligand conjugated to a liposome lysing agent.

11. The product of claim 10 wherein the liposome comprises a phospholipid.

12. A reagent kit for use in an assay for an analyte, comprising:

a package, said package including a binder for at least the analyte; a conjugate comprising a ligand coupled to a liposome lysing agent, said ligand portion of the conjugate being bound by one of the analyte and binder; and liposomes, said binder and said liposomes being supported on separate portions of a solid support said liposomes having a detectable marker therein, and said liposomes being capable of being lysed by said liposome lysing agent.

13. The reagent kit of claim 12 wherein the conjugate is bound to the binder.

14. The reagent kit of claim 12 wherein the lipsomes comprises phospholipid.

15. The reagent kit of claim 12 wherein the solid support is in the form of a dipstick.

16. The reagent kit of claim 12 wherein the conjugate is bound to the binder.

* * * * *